United States Patent
Nobis et al.

(10) Patent No.: US 8,211,114 B2
(45) Date of Patent: Jul. 3, 2012

(54) MEDICAL INSTRUMENT HAVING A MEDICAL SNARE

(75) Inventors: Rudolph H. Nobis, Mason, OH (US); Ifung Lu, Skokie, IL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 552 days.

(21) Appl. No.: 11/409,732

(22) Filed: Apr. 24, 2006

(65) Prior Publication Data
US 2007/0250070 A1    Oct. 25, 2007

(51) Int. Cl.
*A61B 17/24* (2006.01)
*A61B 17/26* (2006.01)

(52) U.S. Cl. ........................ 606/113; 606/114

(58) Field of Classification Search ............ 606/113, 606/170, 148, 41, 585, 47, 159, 114, 110, 606/127, 128, 108; 128/303.14
See application file for complete search history.

(56) References Cited

U.S. PATENT DOCUMENTS

| | | | |
|---|---|---|---|
| 1,225,771 A * | 5/1917 | Clare | 606/113 |
| 2,976,865 A | 3/1961 | Shipley | |
| 3,470,876 A | 10/1969 | Barchilon | |
| 3,521,620 A | 7/1970 | Cook | |
| 3,791,387 A | 2/1974 | Itoh | |
| 3,799,151 A | 3/1974 | Fukaumi et al. | |
| 3,805,791 A | 4/1974 | Seuberth et al. | |
| 4,102,478 A * | 7/1978 | Samoilov | 223/99 |
| 4,326,530 A * | 4/1982 | Fleury, Jr. | 606/47 |
| 4,493,320 A * | 1/1985 | Treat | 606/47 |
| 4,619,247 A | 10/1986 | Inoue et al. | |
| 4,638,802 A | 1/1987 | Okada | |
| 4,735,194 A | 4/1988 | Stiegmann | |
| 4,739,768 A | 4/1988 | Engelson | |
| 4,758,750 A | 7/1988 | Itagaki et al. | |
| 4,791,963 A | 12/1988 | Gronert et al. | |
| 4,884,557 A | 12/1989 | Takehana et al. | |
| 4,890,602 A | 1/1990 | Hake | |
| 4,893,613 A | 1/1990 | Hake | |
| 4,930,494 A | 6/1990 | Takehana et al. | |
| 4,963,147 A | 10/1990 | Agee et al. | |
| 5,002,041 A | 3/1991 | Chikama | |

(Continued)

FOREIGN PATENT DOCUMENTS

DE    4408730    9/1995

(Continued)

OTHER PUBLICATIONS

Ginsberg, G.G., "Colonoscopy with the variable stiffness colonoscope," Gastrointestinal Endoscopy, vol. 58, No. 4 (2003).

(Continued)

*Primary Examiner* — Ryan Severson
*Assistant Examiner* — Tin Nguyen

(57) ABSTRACT

A medical instrument including a resiliently flexible first elongate member and a resiliently flexible second elongate member. The first elongate member has a first proximal end portion and a first distal portion. The second elongate member has a second proximal end portion and a second distal portion, wherein the second distal portion is attached to the first distal portion, and wherein the attached first and second distal portions define a distal-loop medical snare which is insertable within a patient. In a first example, the first proximal end portion is lengthwise translatable with respect to the second proximal end portion to articulate the medical snare. In the same or a second example, the first proximal end portion is rotatable about its centerline to articulate the medical snare.

20 Claims, 4 Drawing Sheets

U.S. PATENT DOCUMENTS

| | | | |
|---|---|---|---|
| 5,035,696 A | 7/1991 | Rydell | |
| 5,066,295 A | 11/1991 | Kozak et al. | |
| 5,078,716 A | 1/1992 | Doll | |
| 5,171,314 A * | 12/1992 | Dulebohn | 606/113 |
| 5,201,732 A | 4/1993 | Parins et al. | |
| 5,201,741 A | 4/1993 | Dulebohn | |
| 5,250,060 A | 10/1993 | Carbo et al. | |
| 5,293,869 A | 3/1994 | Edwards et al. | |
| 5,322,505 A | 6/1994 | Krause et al. | |
| 5,342,299 A | 8/1994 | Snoke et al. | |
| 5,346,504 A | 9/1994 | Ortiz et al. | |
| 5,351,692 A | 10/1994 | Dow et al. | |
| 5,353,807 A | 10/1994 | DeMarco | |
| 5,397,304 A | 3/1995 | Truckai | |
| 5,409,453 A | 4/1995 | Lundquist et al. | |
| 5,431,671 A | 7/1995 | Nallakrishnan | |
| 5,433,721 A | 7/1995 | Hooven et al. | |
| 5,441,499 A | 8/1995 | Fritzsch | |
| 5,482,029 A | 1/1996 | Sekiguchi et al. | |
| 5,522,829 A | 6/1996 | Michalos | |
| 5,531,664 A | 7/1996 | Adachi et al. | |
| 5,531,686 A | 7/1996 | Lundquist et al. | |
| 5,542,948 A * | 8/1996 | Weaver et al. | 606/113 |
| 5,618,294 A | 4/1997 | Aust et al. | |
| 5,628,719 A | 5/1997 | Hastings et al. | |
| 5,706,827 A | 1/1998 | Ehr et al. | |
| 5,728,044 A | 3/1998 | Shan | |
| 5,749,828 A | 5/1998 | Solomon et al. | |
| 5,752,961 A | 5/1998 | Hill | |
| 5,776,080 A | 7/1998 | Thome et al. | |
| 5,792,165 A | 8/1998 | Kileman et al. | |
| 5,810,715 A | 9/1998 | Moriyama | |
| 5,810,807 A | 9/1998 | Ganz et al. | |
| 5,836,947 A | 11/1998 | Fleischman et al. | |
| 5,848,986 A | 12/1998 | Lundquist et al. | |
| 5,865,724 A | 2/1999 | Palmer et al. | |
| 5,897,554 A * | 4/1999 | Chia et al. | 606/41 |
| 5,910,148 A * | 6/1999 | Reimels et al. | 606/144 |
| 5,972,012 A | 10/1999 | Ream et al. | |
| 6,066,102 A | 5/2000 | Townsend et al. | |
| 6,071,277 A | 6/2000 | Farley et al. | |
| 6,074,408 A | 6/2000 | Freeman | |
| 6,093,185 A | 7/2000 | Ellis et al. | |
| 6,093,195 A * | 7/2000 | Ouchi | 606/113 |
| 6,152,918 A | 11/2000 | Padilla et al. | |
| 6,174,280 B1 | 1/2001 | Oneda et al. | |
| 6,203,494 B1 | 3/2001 | Moriyama | |
| 6,352,503 B1 | 3/2002 | Matsui et al. | |
| 6,371,907 B1 | 4/2002 | Hasegawa et al. | |
| 6,395,001 B1 | 5/2002 | Ellman et al. | |
| 6,423,059 B1 | 7/2002 | Hanson et al. | |
| 6,443,943 B1 | 9/2002 | Ouchi | |
| 6,443,944 B1 | 9/2002 | Doshi et al. | |
| 6,450,948 B1 | 9/2002 | Matsuura et al. | |
| 6,451,014 B1 | 9/2002 | Wakikaido et al. | |
| 6,454,703 B1 | 9/2002 | Ide | |
| 6,454,758 B1 | 9/2002 | Thompson et al. | |
| 6,475,222 B1 | 11/2002 | Berg et al. | |
| 6,482,149 B1 | 11/2002 | Torii | |
| 6,488,658 B1 | 12/2002 | Long | |
| 6,500,189 B1 | 12/2002 | Lang et al. | |
| 6,569,105 B1 | 5/2003 | Kortenbach et al. | |
| 6,579,300 B2 | 6/2003 | Griego et al. | |
| 6,602,267 B2 | 8/2003 | Castaneda | |
| 6,612,992 B1 | 9/2003 | Hossack et al. | |
| 6,663,616 B1 | 12/2003 | Roth et al. | |
| 6,663,625 B1 | 12/2003 | Ormsby et al. | |
| 6,689,119 B1 | 2/2004 | DiCaprio et al. | |
| 6,709,388 B1 | 3/2004 | Mosse et al. | |
| 6,730,097 B2 | 5/2004 | Dennis | |
| 6,743,240 B2 | 6/2004 | Smith et al. | |
| 6,764,441 B2 | 7/2004 | Chiel et al. | |
| 6,866,626 B2 | 3/2005 | Long et al. | |
| 7,060,024 B2 | 6/2006 | Long et al. | |
| 7,060,025 B2 | 6/2006 | Long et al. | |
| 7,066,879 B2 | 6/2006 | Fowler et al. | |
| 7,093,518 B2 | 8/2006 | Gmeilbauer | |
| 7,118,587 B2 | 10/2006 | Dycus et al. | |
| 7,441,507 B2 | 10/2008 | Teraura et al. | |
| 7,799,050 B2 | 9/2010 | Hensley et al. | |
| 2001/0029397 A1 | 10/2001 | Thompson | |
| 2001/0037084 A1 | 11/2001 | Nardeo | |
| 2002/0017515 A1 | 2/2002 | Obata et al. | |
| 2002/0087208 A1 | 7/2002 | Koblish et al. | |
| 2002/0095168 A1 | 7/2002 | Griego et al. | |
| 2002/0120178 A1 | 8/2002 | Tartaglia | |
| 2002/0147445 A1 | 10/2002 | Farley et al. | |
| 2002/0177802 A1 | 11/2002 | Moutafis et al. | |
| 2003/0014051 A1 | 1/2003 | Woloszko | |
| 2003/0032863 A1 | 2/2003 | Kazakevich | |
| 2003/0045778 A1 | 3/2003 | Ohline et al. | |
| 2003/0069474 A1 | 4/2003 | Couvillon, Jr. | |
| 2003/0074014 A1 | 4/2003 | Castaneda | |
| 2003/0109898 A1 | 6/2003 | Schwarz et al. | |
| 2003/0125788 A1 | 7/2003 | Long | |
| 2003/0153866 A1 | 8/2003 | Long et al. | |
| 2003/0181785 A1 | 9/2003 | Viebach et al. | |
| 2003/0195492 A1 | 10/2003 | Gobron et al. | |
| 2003/0208219 A1 | 11/2003 | Aznoian et al. | |
| 2004/0034343 A1 | 2/2004 | Gillespie et al. | |
| 2004/0044350 A1 | 3/2004 | Martin et al. | |
| 2004/0068291 A1 | 4/2004 | Suzuki | |
| 2004/0092953 A1 | 5/2004 | Salameh et al. | |
| 2004/0097919 A1 | 5/2004 | Wellman et al. | |
| 2004/0143159 A1 | 7/2004 | Wendlandt | |
| 2004/0143160 A1 | 7/2004 | Couvillon, Jr. | |
| 2004/0193016 A1 | 9/2004 | Root et al. | |
| 2004/0204645 A1 | 10/2004 | Saadat et al. | |
| 2004/0230096 A1 | 11/2004 | Stefanchik et al. | |
| 2005/0043743 A1 * | 2/2005 | Dennis | 606/113 |
| 2005/0154164 A1 | 7/2005 | Tabata | |
| 2005/0183733 A1 | 8/2005 | Kawano et al. | |
| 2005/0203610 A1 | 9/2005 | Tzeng | |
| 2005/0222587 A1 | 10/2005 | Jinno et al. | |
| 2005/0234296 A1 | 10/2005 | Saadat et al. | |
| 2005/0272975 A1 | 12/2005 | McWeeney et al. | |
| 2005/0273084 A1 | 12/2005 | Hinman et al. | |
| 2005/0273085 A1 | 12/2005 | Hinman et al. | |
| 2006/0009711 A1 | 1/2006 | Gingrich et al. | |
| 2006/0089627 A1 | 4/2006 | Burnett et al. | |
| 2007/0225562 A1 | 9/2007 | Spivey et al. | |

FOREIGN PATENT DOCUMENTS

| | | |
|---|---|---|
| DE | 19729499 | 1/1999 |
| EP | 0027704 | 4/1981 |
| EP | 0397489 | 11/1990 |
| EP | 1310206 | 5/2003 |
| EP | 1849421 | 10/2007 |
| JP | 59-181124 | 10/1984 |
| JP | 2004-154164 | 6/2004 |
| WO | WO 96/00030 | 1/1996 |
| WO | 96/10957 | 4/1996 |
| WO | WO 97/12557 | 4/1997 |
| WO | 97/35135 | 9/1997 |
| WO | 99/12489 | 3/1999 |
| WO | 01/08737 | 2/2001 |
| WO | 01/82814 | 11/2001 |
| WO | 01/93938 | 12/2001 |
| WO | 02/43797 | 6/2002 |
| WO | 03/053225 | 7/2003 |
| WO | 03/092476 | 11/2003 |
| WO | 2005/113051 | 12/2005 |
| WO | 2006/019291 | 2/2006 |
| WO | 2006/026687 | 3/2006 |
| WO | 2006/122279 | 11/2006 |

OTHER PUBLICATIONS

Brooker, J.C. et al., "A new variable stiffness colonoscope makes colonoscopy easier: a randomised controlled trial," Gut 2000, 46, pp. 801-805 (2000).

Rex, D.K., "Effect of Variable Stiffness Colonoscopes on Cecal Intubation Times for Routine Colonoscopy by an Experienced Examiner in Sedated Patients," EndoscopY; 33 (1), pp. 60-64 (2001).

Shah, S.G., et al., "Magnetic imaging of colonoscopy: an audit of looping, accuracy and ancillary maneuvers," Gastrointestinal Endoscopy, vol. 52, No. 1, pp. 1-8 (2000).

Shah, S.G., et al., "The variable stiffness colonoscope: assessment of efficacy by magnetic endoscope imaging," Gastrointestinal Endoscopy, vol. 56, No. 2, pp. 195-201 (2002).

"Sensors-Resistance," Smart Engineering Group (1999).

Examination Report, European Application No. 07251728.7 (Dec. 17, 2008).

European Search Report, European Application No. 07251934 (2 pages) (dated Aug. 30, 2007).

EP, Partial Search Report, European Application No. 07251699.0 (Aug. 8, 2007).

EP, Search Report, European Application No. 07251699.0 (Nov. 2, 2007).

CN, Office Action, Chinese Application No. 200710104450.5 (Mar. 9, 2010).

CN, Notification of 2nd Office Action, Chinese Application No. 200710104450.5 (Oct. 28, 2010).

* cited by examiner

MEDICAL INSTRUMENT HAVING A MEDICAL SNARE

FIELD OF THE INVENTION

The present invention is related generally to medical equipment, and more particularly to a medical instrument having a medical snare.

BACKGROUND OF THE INVENTION

Endoscopes (including colonoscopes) are known which have an insertion tube which is insertable within a patient. The insertion tube has an articulatable distal end portion controlled by wires running from the distal end portion to control knobs on the handle of the endoscope. A wide angle video camera in the distal end of the insertion tube permits medical observation. A medical snare assembly is part of a known endoscopic system. A medical snare assembly is known which includes a stainless-steel wire having a lengthwise translatable first end and having a second end which is fixedly attached to the wire after forming a distal-loop medical snare. Another medical snare assembly is known which includes a stainless-steel wire having a lengthwise translatable first end and having a second end which is fixedly attached to a handpiece after forming a distal-loop medical snare. The wire including the distal-loop medical snare is insertable into a working channel of the insertion tube of the endoscope, and the first end is lengthwise translated to extend the medical snare from the distal end portion of the endoscope insertion tube. Then, in one example, the medical snare is used to provide medical treatment by energizing the wire with energy from a radio-frequency generator. Known distal-loop medical snares come in a variety of fixed treatment shapes with a particular treatment shape chosen for a particular application.

Still, scientists and engineers continue to seek improved medical instruments having a medical snare.

SUMMARY OF THE INVENTION

A first expression of an embodiment of the invention is for a medical instrument including a resiliently flexible first elongate member and a resiliently flexible second elongate member. The first elongate member has a first proximal end portion and a first distal portion. The second elongate member has a second proximal end portion and a second distal portion, wherein the second distal portion is attached to the first distal portion, and wherein the attached first and second distal portions define a distal-loop medical snare which is insertable within a patient. The first proximal end portion is lengthwise translatable with respect to the second proximal end portion, wherein lengthwise translation of the first proximal end portion with respect to the second proximal end portion articulates the medical snare. The second proximal end portion is lengthwise translatable with respect to the first proximal end portion, wherein lengthwise translation of the second proximal end portion with respect to the first proximal end portion articulates the medical snare.

A second expression of an embodiment of the invention is for a medical instrument including a resiliently flexible first elongate member and a resiliently flexible second elongate member. The first elongate member has a first proximal end portion and a first distal portion. The second elongate member has a second proximal end portion and a second distal portion, wherein the second distal portion is attached to the first distal portion, and wherein the attached first and second distal portions define a distal-loop medical snare which is insertable within a patient. The first proximal end portion has a centerline and is rotatable about the centerline, wherein rotation of the first proximal end portion about the centerline articulates the medical snare.

Several benefits and advantages are obtained from one or more of the expressions of an embodiment of the invention. In one example, an articulatable medical snare is provided wherein distal lengthwise translation of the first elongate member with respect to the second elongate member articulates the medical snare to a first side, and distal lengthwise translation of the second elongate member with respect to the first elongate member articulates the medical snare to a second side opposite to the first side. In the same or a different example, the distal loop and the medical needle-knife substantially lie in a plane when the distal loop is in a relaxed state, wherein rotation of the first proximal end portion about its centerline articulates the medical snare out of the plane. In the same or a different example, a user lengthwise translates one proximal end portion with respect to the other proximal end portion and/or rotates a proximal end portion about its centerline articulating the medical snare to assume a first treatment shape for a first medical treatment of a patient. In this example, during the same procedure, the user similarly articulates the medical snare to assume a different second treatment shape for a second medical treatment of the patient without having to use two different conventional medical snares having two different fixed treatment shapes. In one application, the medical instrument is inserted into a working channel of a flexible insertion tube of an endoscope, wherein the medical snare can be articulated with respect to the insertion tube of the endoscope allowing independent alignment of the wide angle video camera of the endoscope and the medical snare. In a second application, the medical instrument is adapted to be coupled to, and slid along, an exterior rail of a flexible insertion tube of an endoscope allowing independent alignment of the wide angle video camera of the endoscope and the medical snare.

The present invention has, without limitation, application in hand-activated instruments as well as in robotic-assisted instruments.

DETAILED DESCRIPTION OF THE INVENTION

Figure 1:
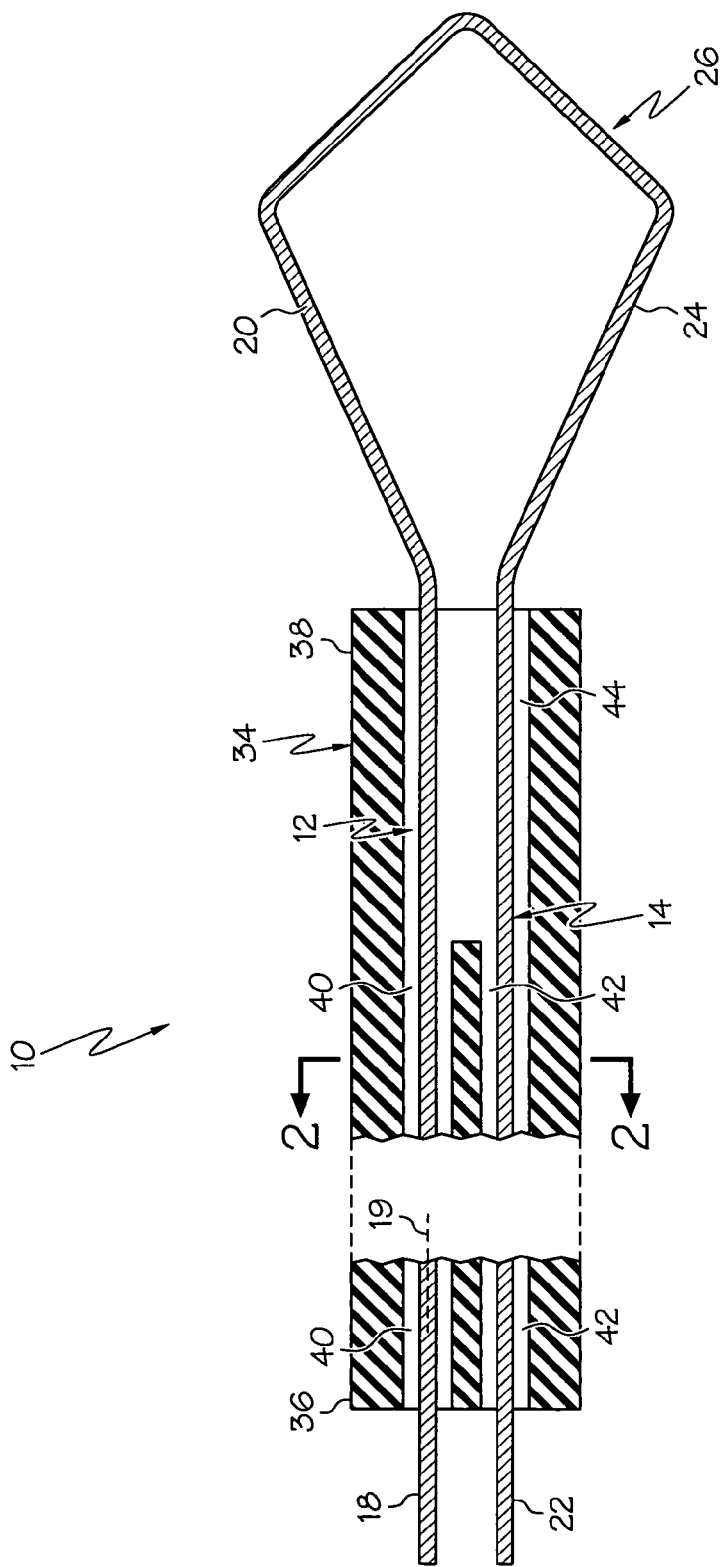
FIG. 1 is a schematic, side elevational, cross sectional view of an embodiment of a medical instrument of the invention showing the distal-loop medical snare of the medical instrument extended from the distal lumen of the shaft of the medical instrument.
Figure 2:
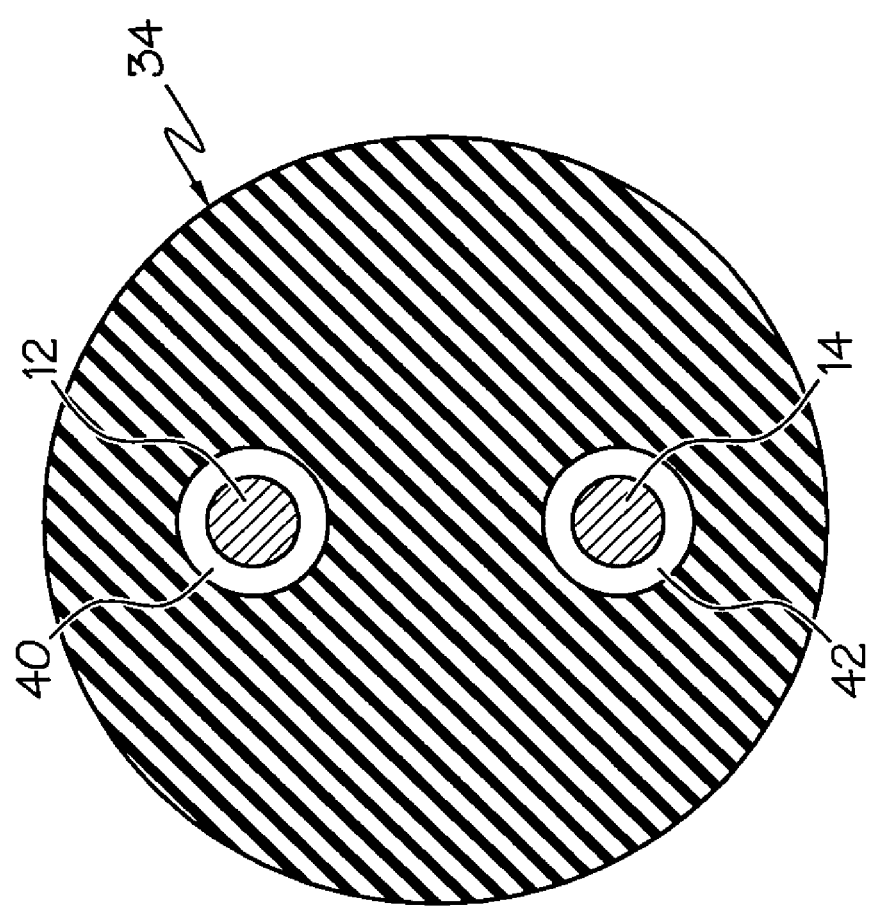
FIG. 2 is a cross sectional view of the medical instrument of FIG. 1 taken along lines 2-2 in FIG. 1.

Before explaining the present invention in detail, it should be noted that the invention is not limited in its application or use to the details of construction and arrangement of parts illustrated in the accompanying drawings and description. The illustrative embodiment of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiment of the present invention for the convenience of the reader and are not for the purpose of limiting the invention.

It is understood that any one or more of the following-described expressions of an embodiment, examples, etc. can be combined with any one or more of the other following-described expressions of an embodiment, examples, etc.

Referring now to the Figures, wherein like numerals represent like elements throughout, FIGS. 1-4 illustrate an embodiment of the invention. A first expression of the embodiment of FIGS. 1-4 is for a medical instrument 10 including a resiliently flexible first elongate member 12 and a resiliently flexible second elongate member 14. The first elongate member 12 has a first proximal end portion 18 and a first distal portion 20. The second elongate member 14 has a second proximal end portion 22 and a second distal portion 24, wherein the second distal portion 24 is attached to the first distal portion 20, and wherein the attached first and second distal portions 20 and 24 define a distal-loop medical snare 26 which is insertable within a patient. The first proximal end portion 18 is lengthwise translatable with respect to the second proximal end portion 22, wherein lengthwise translation of the first proximal end portion 18 with respect to the second proximal end portion 22 articulates the medical snare 26. The second proximal end portion 22 is lengthwise translatable with respect to the first proximal end portion 18, wherein lengthwise translation of the second proximal end portion 22 with respect to the first proximal end portion 18 articulates the medical snare 26.

In one enablement of the first expression of the embodiment of FIGS. 1-4, the second distal portion 24 is monolithically attached to the first distal portion 20. Thus, in this enablement, the first and second distal portions 20 and 24 are two portions of one continuous piece. Non-monolithic attachments are left to the artisan. An example, without limitation, of a resiliently flexible member includes a wire. Types of wire include, without limitation, braided wire, monolithic wire, and wire segments lengthwise attached end to end. Other examples of resiliently flexible members and types of wire are left to those skilled in the art.

In one implementation of the first expression of the embodiment of FIGS. 1-4, the medical snare 26 is a radio-frequency-energized medical snare. Examples of other-energized and non-energized medical snares are left to the artisan.

In one application of the first expression of the embodiment of FIGS. 1-4, the medical snare 26 is insertable within a working channel 30 of an endoscope insertion tube 32.

Figure 3:
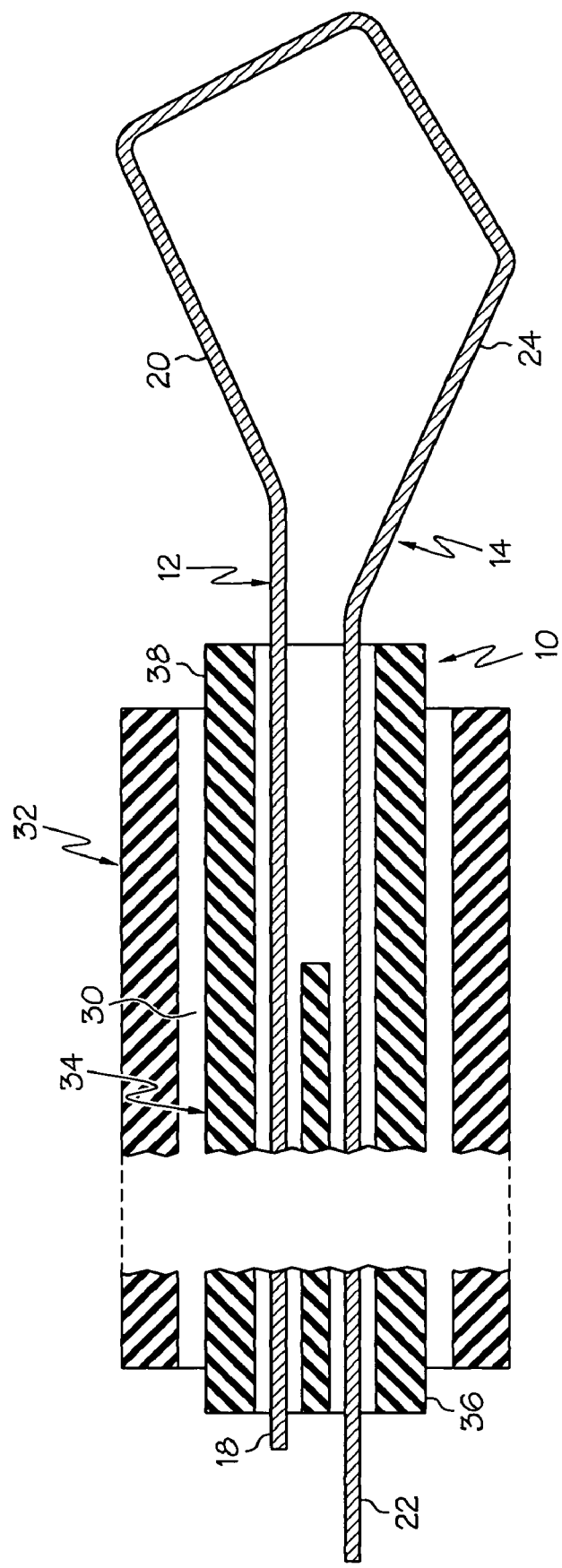
FIG. 3 is a view, as in FIG. 1, but with the medical instrument of FIG. 1 placed within a working channel of an endoscope insertion tube, wherein the distal-loop medical snare is shown extended from the distal lumen of the shaft and articulated to one side, wherein the endoscope handle and operational features (such as insertion tube articulation features and a wide angle video camera) of the endoscope insertion tube have been omitted for clarity.
Figure 4:
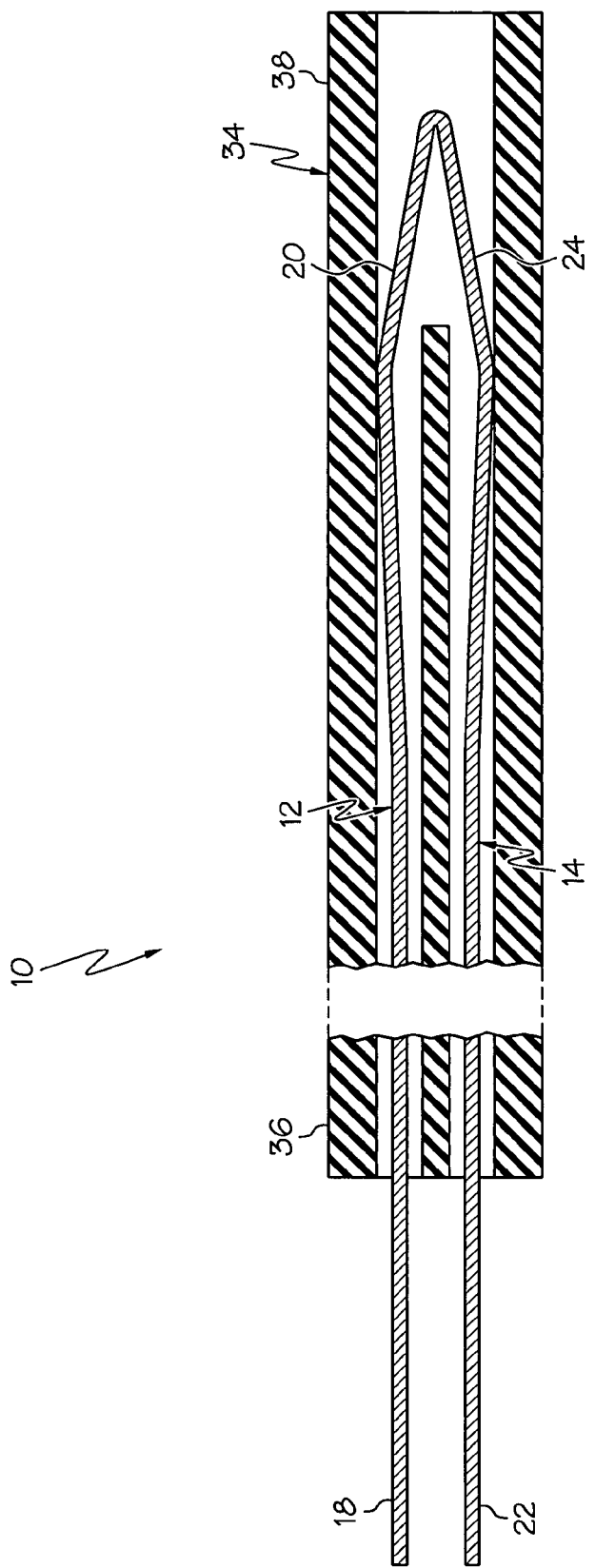
FIG. 4 is a view, as in FIG. 2, but showing the distal-loop medical snare retracted into the distal lumen of the shaft.

In a first choice of materials of the first expression of the embodiment of FIGS. 14, the first and second elongate members 12 and 14 consist essentially of nitinol wire. It is noted that nitinol wire is a superelastic wire having shape memory properties wherein the nitinol wire can have a desired shape set into the wire and wherein after flexing the wire, the wire will resiliently return to its set shape, as is known to those skilled in the art. It is noted that the medical snare 26 has a relaxed state (i.e., a state wherein the medical snare 26 it is not subject to a force and wherein the medical snare is not subject to a torque). In a first example, FIG. 1 illustrates the relaxed state wherein the medical snare 26 has a symmetrical first treatment shape which is a desired shape set into the wire. FIG. 3 shows the result of a user lengthwise translating one proximal end portion with respect to the other proximal end portion articulating the medical snare 26 to assume a different asymmetrical second treatment shape. Applicants have found that a kite shape of the medical snare 26 improves the articulation of the medical snare 26. It is noted that a kite shape is a diamond shape having two shorter sides extending from the top (distal) vertex of the diamond shape and having two longer sides extending from the bottom (proximal) vertex of the diamond shape.

A second expression of the embodiment of FIGS. 1-4 is for a medical instrument 10 including a resiliently flexible first elongate member 12 and a resiliently flexible second elongate member 14. The first elongate member 12 has a first proximal end portion 18 and a first distal portion 20. The second elongate member 14 has a second proximal end portion 22 and a second distal portion 24, wherein the second distal portion 24 is attached to the first distal portion 20, and wherein the attached first and second distal portions 20 and 24 define a distal-loop medical snare 26 which is insertable within a patient. The first proximal end portion 18 has a centerline 19 and is rotatable about the centerline 19, wherein rotation of the first proximal end portion 18 about the centerline 19 articulates the medical snare 26.

In one illustration of the first expression of the embodiment of FIGS. 1-4, the second proximal end portion 22 is not rotatable about its centerline. In a different illustration, the second proximal end portion 22 is rotatable about its centerline. In one modification, both the first and second proximal end portions are rotatable in the same direction about their corresponding centerlines.

It is noted that the enablements, implementations, applications, etc. of the first expression of the embodiment of FIGS. 1-4 are equally applicable to the second expression of the embodiment of FIGS. 1-4. In one employment of the second expression of the embodiment of FIGS. 1-4, the first proximal end portion 18 is lengthwise translatable with respect to the second proximal end portion 22, wherein lengthwise translation of the first proximal end portion 18 with respect to the second proximal end portion 22 articulates the medical snare 26. In the same or a different employment, the second proximal end portion 22 is lengthwise translatable with respect to the first proximal end portion 18, wherein lengthwise translation of the second proximal end portion 22 with respect to the first proximal end portion 18 articulates the medical snare 26.

A third expression of the embodiment of FIGS. 1-4 is for a medical instrument 10 including a resiliently flexible first elongate member 12, a resiliently flexible second elongate member 14, and a flexible shaft 34. The first elongate member 12 has a first proximal end portion 18 and a first distal portion 20. The second elongate member 14 has a second proximal end portion 22 and a second distal portion 24, wherein the second distal portion 24 is attached to the first distal portion 20, and wherein the attached first and second distal portions 20 and 24 define a distal-loop medical snare 26 which has a shape. The first proximal end portion 18 is lengthwise translatable with respect to the second proximal end portion 22, and the second proximal end portion 22 is lengthwise translatable with respect to the first proximal end portion 18. The shaft 34 has proximal and distal shaft ends 36 and 38, first and second proximal lumens 40 and 42, and a distal lumen 44. The distal shaft end 38 is insertable within a patient. The first and second proximal lumens 40 and 42 extend from the proximal shaft end 36 toward the distal shaft end 38. The distal lumen 44 extends from the distal shaft end 38 toward the proximal shaft end 36 and is in communication with each of the first and second proximal lumens 40 and 42. The first elongate member 12 is located in the first proximal lumen 40, and the second elongate member 14 is located in the second proximal lumen 42. The medical snare 26 is retractable into the distal lumen 44 and is extendable from the distal lumen 44. Lengthwise translation of the first proximal end portion 18 with respect to the second proximal end portion 22 articulates the medical snare 26 changing the shape when the medical snare 26 has been extended from the distal lumen 44. Lengthwise translation of the second proximal end portion 22 with respect to the first proximal end portion 18 articulates the medical snare 26 changing the shape when the medical snare 26 has been extended from the distal lumen 44.

It is noted that the first and second elongate members 12 and 14 are slidingly disposed in the corresponding ones of the first and second proximal and the distal lumens 40, 42 and 44. Simultaneous distal translation of both the first and second proximal end portions 18 and 22 extends the medical snare 26 from the distal lumen 44. Simultaneous proximal translation of both the first and second proximal end portions 18 and 22 retracts the medical snare 26 into the distal lumen 44.

In one application of the third expression of the embodiment of FIGS. 1-4, the shaft 34 is insertable within a working channel 30 of an endoscope insertion tube 32. It is noted that the other enablements, implementations, etc. of the first expression of the embodiment of FIGS. 1-4 are equally applicable to the third expression of the embodiment of FIGS. 1-4.

A fourth expression of the embodiment of FIGS. 1-4 is for a medical instrument 10 including a resiliently flexible first elongate member 12, a resiliently flexible second elongate member 14, and a flexible shaft 34. The first elongate member 12 has a first proximal end portion 18 and a first distal portion 20. The second elongate member 14 has a second proximal end portion 22 and a second distal portion 24, wherein the second distal portion 24 is attached to the first distal portion 20, and wherein the attached first and second distal portions 20 and 24 define a distal-loop medical snare 26 which has a shape. The first proximal end portion 18 has a centerline 19 and is rotatable about the centerline 19. The shaft 34 has proximal and distal shaft ends 36 and 38, first and second proximal lumens 40 and 42, and a distal lumen 44. The distal shaft end 38 is insertable within a patient. The first and second proximal lumens 40 and 42 extend from the proximal shaft end 36 toward the distal shaft end 38. The distal lumen 44 extends from the distal shaft end 38 toward the proximal shaft end 36 and is in communication with each of the first and second proximal lumens 40 and 42. The first elongate member 12 is located in the first proximal lumen 40, and the second elongate member 14 is located in the second proximal lumen 42. The medical snare 26 is retractable into the distal lumen 44 and is extendable from the distal lumen 44. Rotation of the first proximal end portion 18 about the centerline 19 articulates the medical snare 26 changing the shape when the medical snare 26 has been extended from the distal lumen 44.

In one application of the fourth expression of the embodiment of FIGS. 1-4, the shaft 34 is insertable within a working channel 30 of an endoscope insertion tube 32. It is noted that the other enablements, implementations, employments etc. of the second expression of the embodiment of FIGS. 1-4 are equally applicable to the fourth expression of the embodiment of FIGS. 1-4. In one variation, the second proximal end portion is not rotatable about its centerline. In a different variation, the second proximal end portion is rotatable about its centerline. In one modification, both the first and second proximal end portions are rotatable in the same direction about their corresponding centerlines.

In another application, not shown, of the third and/or fourth expressions of the embodiment of FIGS. 1-4, the shaft has a rail-coupling feature adapted to be coupled to, and slid along, an exterior rail of a flexible insertion tube of an endoscope. Other applications, including non-endoscope use of the medical instrument 10, are left to those skilled in the art. In a first choice of materials of the third and/or fourth expressions of the embodiment of FIGS. 1-4, the shaft 34 comprises an elastomer.

In one extension of any one or more or all of the previously described expressions of the embodiment of FIGS. 1-4, the medical instrument 10 includes a handpiece, not shown. In one example, the handpiece includes a joystick-type handle operatively connected to the first proximal end portion 18 of the first elongate member 12 and to the second proximal end portion 22 of the second elongate member 14, wherein moving the joystick handle to one side articulates the medical snare 26 to one side and moving the joystick handle to the other side articulates the medical snare 26 to the other side, wherein the first proximal end portion 18 of the first elongate member 12 has a square cross section, and wherein rotation of a ring on the handpiece rotates the first proximal end portion 18 inside the handpiece through a gear arrangement. In another example, not shown, the handpiece has one stationary finger ring for support and has first and second slidable finger rings connected to a corresponding one of the first and second proximal end portions 18 and 22 for lengthwise translation thereof, wherein the first proximal end portion 18 of the first elongate member 12 has a square cross section, and wherein rotation of a ring on the handpiece rotates the first proximal end portion 18 inside the handpiece through a gear arrangement. Other examples of handpieces and robotic operation of the medical instrument 10 are left to those skilled in the art. In a different employment, a user manually translates and/or rotates the first and/or second proximal end portions 18 and 22 of the first and/or second elongate members 12 and 14 to articulate the medical snare 26.

In one procedure involving the third and/or fourth expressions of the embodiment of FIGS. 1-4, both the first and second proximal end portions 18 and 22 are lengthwise translated to retract the medical snare 26 within the distal lumen 44 before the shaft 34 is inserted within a patient (such as before the shaft 34 is inserted within a working channel 30 of an endoscope insertion tube 32 which has been inserted within a patient). When the distal shaft end 38 has been positioned proximate the target tissue requiring medical treatment, both the first and second proximal end portions 18 and 22 are lengthwise translated to extend the medical snare 26 from the distal lumen 44 (and from the endoscope insertion tube 32, if present). Thereafter, the medical snare 26 is articulated to a desired orientation and/or shape for medical treatment.

Several benefits and advantages are obtained from one or more of the expressions of an embodiment of the invention. In one example, an articulatable medical snare is provided wherein distal lengthwise translation of the first elongate member with respect to the second elongate member articulates the medical snare to a first side, and distal lengthwise translation of the second elongate member with respect to the first elongate member articulates the medical snare to a second side opposite to the first side. In the same or a different example, the distal loop and the medical needle-knife substantially lie in a plane when the distal loop is in a relaxed state, wherein rotation of the first proximal end portion about its centerline articulates the medical snare out of the plane. In the same or a different example, a user lengthwise translates one proximal end portion with respect to the other proximal end portion and/or rotates a proximal end portion about its centerline articulating the medical snare to assume a first treatment shape for a first medical treatment of a patient. In this example, during the same procedure, the user similarly articulates the medical snare to assume a different second treatment shape for a second medical treatment of the patient without having to use two different conventional medical snares having two different fixed treatment shapes. In one application, the medical instrument is inserted into a working channel of a flexible insertion tube of an endoscope, wherein the medical snare can be articulated with respect to the insertion tube of the endoscope allowing independent alignment of the wide angle video camera of the endoscope and the medical snare. In a second application, the medical instrument is adapted to be coupled to, and slid along, an exterior rail of a flexible insertion tube of an endoscope allowing independent alignment of the wide angle video camera of the endoscope and the medical snare.

While the present invention has been illustrated by a description of several expressions of an embodiment, it is not the intention of the applicants to restrict or limit the spirit and scope of the appended claims to such detail. Numerous other variations, changes, and substitutions will occur to those skilled in the art without departing from the scope of the invention. For instance, the medical instrument of the invention has application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended Claims.

What is claimed is:

1. A medical instrument comprising:
a) a flexible shaft having first and second proximal lumens;
b) a resiliently flexible first elongate member disposed in the first proximal lumen and having a first proximal end portion and a first distal portion;
c) a resiliently flexible second elongate member disposed in the second proximal lumen and having a second proximal end portion and a second distal portion, wherein the second distal portion is attached to the first distal portion, wherein the attached first and second distal portions define an open distal-loop medical snare which has a relaxed, set shape of truncated diamond form, with two shorter sides extending proximally from a distal vertex of the shape, and two longer sides extending distally from proximate a proximal vertex of the shape, the two longer sides being unattached proximate the proximal vertex of the shape; and
d) a handpiece having a mechanism operatively connected to the first proximal end portion of the first elongate member and to the second proximal end portion of the second elongate member, wherein operation of the mechanism lengthwise translates the first proximal end portion with respect to the second proximal end portion, the mechanism including a ring rotating the first proximal end portion inside the handpiece through a gear arrangement; wherein the first proximal end portion is not attached to the second proximal end portion such that the first proximal end portion is lengthwise translatable with respect to the second proximal end portion, wherein lengthwise translation of the first proximal end portion with respect to the second proximal end portion articulates the medical snare, wherein the second proximal end portion is lengthwise translatable with respect to the first proximal end portion, wherein lengthwise translation of the second proximal end portion with respect to the first proximal end portion articulates the medical snare, wherein the first proximal end portion has a longitudinal centerline and is rotatable about the longitudinal centerline with respect to the flexible shaft, and wherein rotation of the first proximal end portion about the longitudinal centerline with respect to the flexible shaft articulates the medical snare.

2. The medical instrument of claim 1, wherein the second distal portion is monolithically attached to the first distal portion.

3. The medical instrument of claim 1, wherein the medical snare is a radio-frequency-energized medical snare.

4. The medical instrument of claim 1, wherein the medical snare is insertable within a working channel of an endoscope insertion tube.

5. The medical instrument of claim 1, wherein the mechanism includes a joystick-type handle.

6. The medical instrument of claim 1, wherein the mechanism includes first and second slidable finger rings connected to corresponding ones of the first and second proximal end portions of the first and second elongate members.

7. A medical instrument comprising:
a) a flexible shaft;
b) a resiliently flexible first elongate member having a first proximal end portion and a first distal portion;
c) a resiliently flexible second elongate member having a second proximal end portion and a second distal portion, wherein the second distal portion is attached to the first distal portion, wherein the attached first and second distal portions define an open distal-loop medical snare which has a relaxed, set shape of truncated diamond form, with two shorter sides extending proximally from a distal vertex of the shape, and two longer sides extending distally from proximate a proximal vertex of the shape, the two longer sides being unattached proximate the proximal vertex of the shape; and
d) a handpiece having a mechanism operatively connected to the first proximal end portion of the first elongate member and to the second proximal end portion of the second elongate member, the mechanism including a ring rotating the first proximal end portion inside the handpiece through a gear arrangement; wherein the first proximal end portion is not attached to the second proximal end portion such that the first proximal end portion has a longitudinal centerline and is rotatable about the longitudinal centerline with respect to the flexible shaft, and wherein rotation of the first proximal end portion about the longitudinal centerline with respect to the flexible shaft articulates the medical snare.

8. The medical instrument of claim 7, wherein operation of the mechanism lengthwise translates the first proximal end portion with respect to the second proximal end portion, wherein the first proximal end portion is lengthwise translatable with respect to the second proximal end portion, and wherein lengthwise translation of the first proximal end portion with respect to the second proximal end portion articulates the medical snare.

9. The medical instrument of claim 7, wherein the second distal portion is monolithically attached to the first distal portion.

10. The medical instrument of claim 7, wherein the medical snare is a radio-frequency-energized medical snare.

11. The medical instrument of claim 7, wherein the medical snare is insertable within a working channel of an endoscope insertion tube.

12. A medical instrument comprising:
a) a resiliently flexible first elongate member having a first proximal end portion and a first distal portion;
b) a resiliently flexible second elongate member having a second proximal end portion and a second distal portion, wherein the second distal portion is attached to the first distal portion, wherein the first and second elongate members consist essentially of nitinol wire, wherein the attached first and second distal portions define an open distal-loop medical snare which has a relaxed, set shape of truncated diamond form, with two shorter sides extending proximally from a distal vertex of the shape, and two longer sides extending distally from proximate a proximal vertex of the shape, the two longer sides being unattached proximate the proximal vertex of the shape, wherein the first proximal end portion is lengthwise translatable with respect to the second proximal end portion, and wherein the second proximal end portion is lengthwise translatable with respect to the first proximal end portion;
c) a flexible shaft having a proximal shaft end, a distal shaft end insertable within a patient, first and second proximal lumens extending from the proximal shaft end toward the distal shaft end, and a distal lumen extending from the distal shaft end toward the proximal shaft end and in communication with each of the first and second proximal lumens, wherein the first elongate member is disposed in the first proximal lumen, wherein the second elongate member is disposed in the second proximal lumen, and wherein the medical snare is retractable into the distal lumen and is extendable from the distal lumen; and
d) a handpiece having a mechanism operatively connected to the first proximal end portion of the first elongate member and to the second proximal end portion of the second elongate member, wherein operation of the mechanism lengthwise translates the first proximal end portion with respect to the second proximal end portion;
wherein lengthwise translation of the first proximal end portion with respect to the second proximal end portion articulates the medical snare changing the shape when the medical snare has been extended from the distal lumen, and wherein lengthwise translation of the second proximal end portion with respect to the first proximal end portion articulates the medical snare changing the shape when the medical snare has been extended from the distal lumen.

13. The medical instrument of claim 12, wherein the second distal portion is monolithically attached to the first distal portion.

14. The medical instrument of claim 12, wherein the shaft is insertable within a working channel of an endoscope insertion tube.

15. The medical instrument of claim 12, wherein the first proximal end portion is not attached to the second proximal end portion.

16. A medical instrument comprising:
a) a resiliently flexible first elongate member having a first proximal end portion and a first distal portion;
b) a resiliently flexible second elongate member having a second proximal end portion and a second distal portion, wherein the second distal portion is attached to the first distal portion, wherein the first and second elongate members consist essentially of nitinol wire, wherein the attached first and second distal portions define an open distal-loop medical snare which has a relaxed, set shape of truncated diamond form, with two shorter sides extending proximally from a distal vertex of the shape, and two longer sides extending distally from proximate a proximal vertex of the shape, the two longer sides being unattached proximate the proximal vertex of the shape, and wherein the first proximal end portion has a longitudinal centerline and is rotatable about the centerline with respect to a flexible shaft, wherein the flexible shaft has a proximal shaft end, a distal shaft end insertable within a patient, first and second proximal lumens extending from the proximal shaft end toward the distal shaft end, and a distal lumen extending from the distal shaft end toward the proximal shaft end and in communication with each of the first and second proximal lumens, wherein the first elongate member is disposed in the first proximal lumen, wherein the second elongate member is disposed in the second proximal lumen, wherein the medical snare is retractable into the distal lumen and is extendable from the distal lumen; and
c) a handpiece having a mechanism operatively connected to the first proximal end portion of the first elongate member and to the second proximal end portion of the second elongate member, the mechanism including a ring rotating the first proximal end portion inside the handpiece through a gear arrangement;
wherein rotation of the first proximal end portion about the longitudinal centerline with respect to the flexible shaft articulates the medical snare changing the shape when the medical snare has been extended from the distal lumen.

17. The medical instrument of claim 16, wherein operation of the mechanism lengthwise translates the first proximal end portion with respect to the second proximal end portion, wherein the first proximal end portion is lengthwise translatable with respect to the second proximal end portion, wherein lengthwise translation of the first proximal end portion with respect to the second proximal end portion articulates the medical snare changing the shape, wherein the second proximal end portion is lengthwise translatable with respect to the first proximal end portion, and wherein lengthwise translation of the second proximal end portion with respect to the first proximal end portion articulates the medical snare changing the shape.

18. The medical instrument of claim 16, wherein the second distal portion is monolithically attached to the first distal portion.

19. The medical instrument of claim 16, wherein the shaft is insertable within a working channel of an endoscope insertion tube.

20. The medical instrument of claim 16, wherein the first proximal end portion is not attached to the second proximal end portion.

* * * * *